United States Patent [19]
Sano et al.

[11] 3,967,932
[45] July 6, 1976

[54] RAPID ANALYSIS OF CATION CONTAINED IN LIQUID

[75] Inventors: Takezo Sano, Takatsuki; Akira Kobayashi, Ibaragi, both of Japan

[73] Assignee: Sumitomo Chemical Company, Limited, Osaka, Japan

[22] Filed: Oct. 10, 1975

[21] Appl. No.: 621,344

[52] U.S. Cl. .......................... 23/230 R; 23/253 TP; 210/38 B
[51] Int. Cl.² .............. G01N 31/04; G01N 23/223; G01N 23/10
[58] Field of Search ............... 23/230 R, 253 TP; 210/38 B, 502, 505; 73/61.1 R

[56] References Cited
UNITED STATES PATENTS

| | | | |
|---|---|---|---|
| 3,155,454 | 11/1964 | Salutsky et al. | 210/38 B |
| 3,408,291 | 10/1968 | Thomas et al. | 210/38 B |

OTHER PUBLICATIONS
Campbell et al., "Micro and Trace Analysis by a Combination of Ion Exchange Resin-Loaded Papers and X-Ray Spectrography," Anal. Chem. vol. 38, July, 1966, pp. 987–996.

Primary Examiner—R.E. Serwin
Attorney, Agent, or Firm—Stevens, Davis, Miller & Mosher

[57] ABSTRACT

A method for the rapid analysis of a cation contained in a liquid, which comprises filtering a liquid sample through a cation exchange filter paper having a high rate of ion exchange, which was made from fibers having cation exchange functional groups, thus collecting substantially the entire amount of the cation contained in said liquid sample in the top surface layer of said filter paper, and analyzing the cation-loaded filter paper as such or the eluate obtained by elution of the cation to be analyzed from said cation-loaded filter paper, to determine the cation.

12 Claims, 2 Drawing Figures

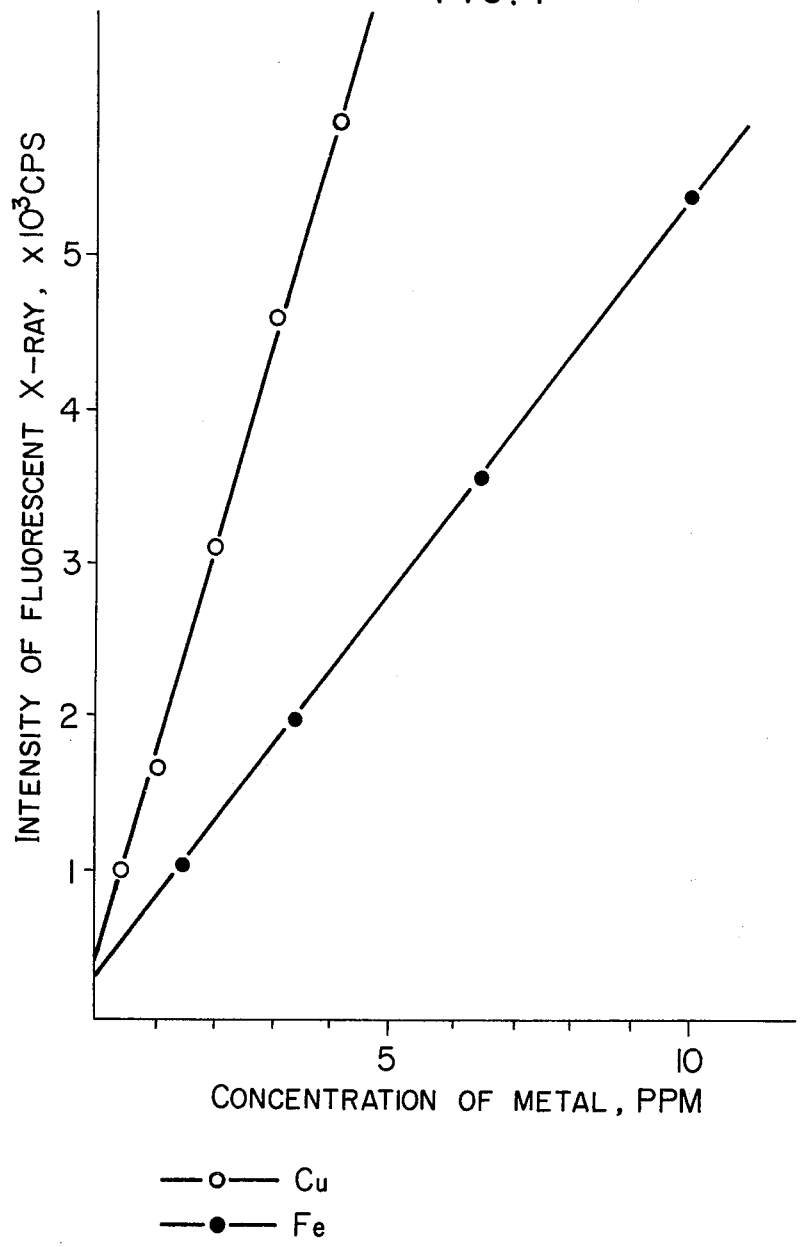

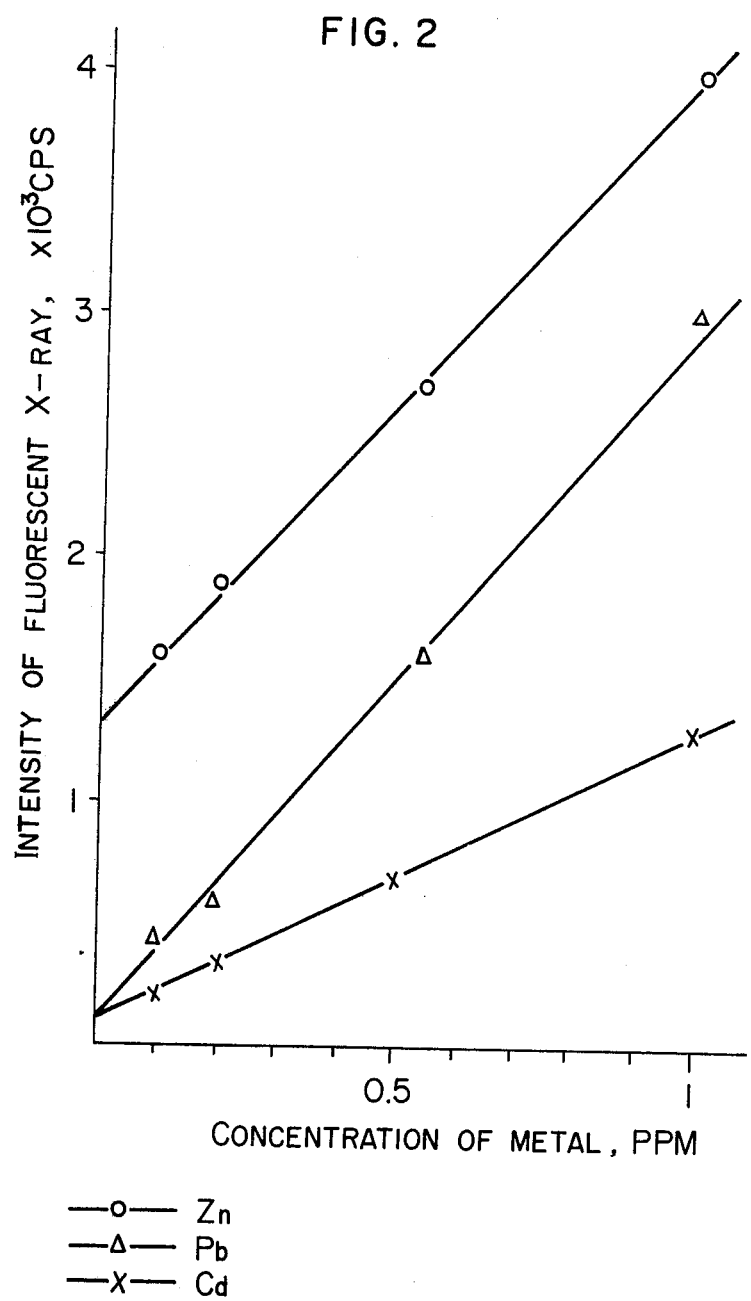

RAPID ANALYSIS OF CATION CONTAINED IN LIQUID

This invention relates to a rapid and high-sensitivity method for analyzing a cation contained in a liquid, using an ion exchange filter paper.

In recent years, in connection with the waste water analysis, water quality control, and trace analysis for valuable components, there has been aroused a great need for sensitive and rapid analytical methods. With the progress in development and improvement of analytical instruments, it has become possible to utilize sensitive instruments such as X-ray fluorescence spectrometer, atomic absorption spectrophotometer, polarograph, etc. Nevertheless, when a component contained in trace amounts in a liquid such as aqueous solution is to be analyzed, the liquid cannot be fed as such to the above-noted instrument in view of sensitivity, but must be subjected to a tedious pretreatment of concentrating the solution, which is prone to error. Such a concentration treatment is particularly necessary to make up for deficiency in sensitivity of the analytical tool and has been conventionally carried out by evaporation or by adsorption-elution with an ion exchange resin, either of which is considerably time-consuming and requires the greatest care in actual practice. As a result of continued investigation to improve the disadvantages of prior art, the present inventors and others have succeeded in developing a cation exchange filter paper made from fibers containing cation exchange functional groups and found that said filter paper has a far greater rate of ion exchange than those of conventonal ion exchange resins. It was further found that when a solution containing trace amounts of a cation to be determined is passed through this filter paper, substantially entire amount of said cation is adsorbed by the top surface layer of the filter paper and that it is possible to carry out a rapid, simplified, and high-sensitivity quantitative or qualitative analysis of cations either by subjecting said cation-loaded filter paper directly to the X-ray fluorescence spectrophotometry, activation analysis, or the like, or by eluting the adsorbed cation with a strong acid to obtain a concentrated solution of said cation and subjecting the resulting solution to the atomic absorption spectrophotometry or polarography or the like.

There has been known, heretofore, a method bearing some resemblance to the present method, which comprises keeping an ion exchange membrane or a filter paper comprising a finely powdered ion exchange resin and fibers in contact with a solution containing an ion to be determined for a period of time sufficient enough to effect the equilibrium adsorption and thereafter subjecting the membrane or filter paper to, for example, the X-ray fluorescence spectrophotometry. The said known method, however, requires a long time and troublesome procedure for the equilibrium adsorption and, moreover, is affected by coexisting ions and pH of the solution, rendering the method unpracticable. Such disadvantages are due to insufficient ability of the membrane or filter paper to collect ions.

An object of this invention is to provide a novel, rapid, and sensitive method for the analysis of a cation contained in a liquid, whereby the aforesaid disadvantages are eliminated.

This invention is characterized by filtering a liquid sample through a cation exchange filter paper having a high rate of ion exchange, which was made from fibers having cation exchange functonal groups, thus collecting substantially entire amount of the cations contained in said sample in the top surface layer of said filter paper, and analyzing the cation-loaded filter paper as such or after having been dried or, alternatively, analyzing the eluate obtained by elution of the cation to be analyzed from said cation-loaded filter paper.

The cation exchange filter paper for use in the present method is that made from fibers having cation exchange functional groups such as sulfonic acid, carboxylic acid, phosphonic acid, sulfate ester, and phosphate ester groups.

The fibers to be used as starting material are synthetic pulps such as those made by the known process from, for example, polyethylene, polypropylene, polystyrene, polyvinyl chloride, and the like, and natural cellulose pulp. With respect to resistance against acids and alkalis, synthetic pulp is preferred. Introduction of functional groups into fiber can be effected by known polymer reactions and grafting techniques.

The present filter paper can be made in several ways, but most simply and conveniently by an ordinary paper-making process. By selecting a pulp whose unit fiber has a diameter of 0.5 to 100 $\mu$, it is possible to obtain a cation exchange filter paper of sufficient strength and having a high rate of ion exchange with the cation to be analyzed. In making the filter paper from a pulp, other types of pulp may be blended to control strength and filtration rate of the filter paper. It is also possible to increase the strength by use of a binding material.

The cation exchange capacity depends on the number of introduced functional groups and is preferably in the range from 0.1 to 10 meq/g. If it is below 0.1 meq/g, sufficient amount of the cation to be analyzed cannot be collected; whereas if the capacity is beyond 10 meq/g, the fiber tends to become degraded. In case such an accompanied disadvantage would not arise, an ion exchange capacity exceeding 10 meq/g has no harmful effect.

It is desirable that the cation exchange filter paper is resistant to acids, alkalis, and solvents and has a strength sufficient to withstand the filtration procedure and a high dimensional stability. A suitable water permeability of the filter paper is about 1 to about 1,000 seconds, preferably 5 to 100 seconds, in terms of filtration time required to filter 1 cc of water under a head of 10 cm Aq through 1 cm$^2$ of filter paper. A filter paper having an excessively large filtration rate is undesirable, because an unsatisfactory collection of the objective cation would occur locally.

The cation exchange filter paper thus obtained is able to collect the objective cation satisfactorily at a space velocity about 50 to 200 times as large as that of an ordinary ion exchange resin.

For example, such a filter paper may be obtained, as has already been disclosed by the present inventors in Japanese Patent Application Laid-open No. 56,387/75, by making paper from a sulfonated polyethylene pulp. As disclosed in said Patent Application a filter paper excellent in strength and dimensional stability is obtained by making paper from a sulfonated polyethylene pulp blended with small amounts of untreated polyethylene pulp and subjecting the resulting paper to some degrees of heat treatment. Being excellent in resistances to acids, alkalis, and solvents, this filter paper is suitable for the method of this invention. Although not critical, the thickness of the filter paper is preferably in the range from 0.1 to 5 mm in view of economy and convenience in handling.

The present analytical method can be applied to any sample in the form of liquid such as aqueous solution or a solution in organic solvents, even when the sample contains a small amount of suspended solid or emulsified matter. In such a case, using the performance characteristics of the present filter paper to advantage, the suspended solid can be collected simultaneously with the dissolved cation and analyzed separately. An alternative procedure is to collect separately the insoluble matter and the dissolved cation in single filtration step by filtering the sample through an ordinary filter paper placed upon the cation exchange filter paper and to analyze the collected components separately in parallel.

Cations other than hydrogen cation are collectable by the cation exchange filter paper. collectability depends upon the type of functional groups introduced into the filter paper. By proper selection of functional groups, cations of the following metals can be collected: alkali metals such as, for example, sodium, potassium, and lithium, alkaline earth metals such as, for example, magnesium, calcium, strontium and barium; boron; aluminum; heavy metals such as, for example, titanium, vanadium, chromium, manganese, iron, cobalt, nickel, copper, zinc, zirconium molybdenum, tungsten, silver, gold, mercury, cadmium, tin, lead, platinum, and palladium. When present in an aqueous solution, these metals should be in the form of cation. If these metals are in the form of anion of an oxoacid such as aluminic acid, chromic acid, or the like, it is necessary to change the form into that of cation by suitable pretreatments. In the analysis of cations of these metals in an aqueous solution, the present method is not affected by the presence of a water-soluble organic solvent such as, for example, methanol, ethanol, or acetone or by the presence of an water-insoluble oil in the form of emulsion. Accordingly, the present method is applicable to a sample of ordinary waste water or the like as such.

The filtration procedure for the collection of cations is decribed below in detail.

According to the type of cation to be analyzed, a cation exchange filter paper bearing proper functional groups capable of collecting the objective cation is selected. To collect the cation, the sample liquid is passed through the filter paper mounted on a filter holder at a space velocity [linear velocity (cm/hr)/thickness (cm)] of 1 to 10,000 $hr^{-1}$, preferably 10 to 2,000 $hr^{-1}$. The amount of the objective cation in the sample liquid should be controlled below the total ion exchange capacity of the filter paper. It is safe to control the amount of sample liquid passed through the filter paper in such a manner that the amount of cations to be collected may not exceed one-third, preferably one-tenth of the ion exchange capacity of the filter paper. The increase in the quantity of sample liquid passed through the filter paper is effective in increasing the concentration degree and, hence, the sensitivity of the analysis, but accompanies a disadvantage of prolonged analysis time. By taking these factors into consideration, the flow time of the sample solution is kept within one hour, preferably within 10 minutes, said flow time being for shorter than those required in conventional methods.

The cation collected on the filter paper can be analyzed by any of the following techniques:
1. Elementary analysis after drying;
2. X-ray fluorescence analysis after drying;
3. Emission spectroscopic analysis after drying;
4. Measurement of radioactivity of the cation as collected on the filter paper (trace analysis of radioactive constituent);
5. Radio activation analysis after drying;
6. Reflective infrared analysis after drying;
7. Atomic absorption analysis after elution;
8. Polarography after elution;
9. Visible and ultraviolet spectroscopic analysis after elution;
10. Polarimetry after elution;
11. Nuclear magnetic resonance spectral analysis after elution.

Other combinations than those mentioned above are also possible. Of the above-mentioned analytical techniques, those of (2), (5), (7), and (8) are preferred by reason of sensitivity and rapidity of the analysis and particularly the techniques (2) and (7) are very useful because these make it possible to analyze far smaller amount of the objective cation in far shorter time, as compared with conventional methods, by use of the same instruments as conventionally used.

Especially the technique (2) enables the present method to exhibit its advantages to maximum extent. Since the cation exchange filter paper used in the present method has an extremely high rate of ion exchange, it is possible to further increase adsorption of the objective cation to top surface layer of the filter paper by selecting a relatively low level (below 1000 $hr^{-1}$) in the space velocity of sample liquid. As the result, when the dried filter paper loaded with objective cation is analyzed by the X-ray fluorescence technique, a linear relationship holds between the concentration of the objective cation in the sample liquid and the intensity of X-ray fluorescence ("CPS": Counts per second) over a wide range of cation concentration. Consequently, a quantitative analysis becomes possible by use of a calibration curve without applying any complicated correction. The sensitivity of detection is the order of 1 ppb. Another advantage is in that simultaneous analysis of multiple components is possible. Accordingly, the present method is conveniently applicable to the analysis of water containing multiple cations to be analyzed, such as water for various uses or waste water, and no particular correction is necessary in computing the analytical data because of minor effect of coexisting cations on one another.

General advantages of the present method may be summarized as follows:

First, owing to a markedly high rate of ion exchange of the cation exchange filter paper, the objective cation present in trace amounts in a large volume of liquid can be collected rapidly and completely. Accordingly, the sample liquid can be immediately filtered on the sampling spot to collect the objective cation rapidly and completely, thus saving the time and labor required to carry a large quantity of the liquid to an analytical laboratory. Secondly, because of a high collection capacity of the top surface layer, the filter paper loaded with the objective cation can be analyzed as such by the X-ray fluorescence technique to obtain analytical results with excellent rapidity and convenience. In this case, high-sensitivity analysis and simultaneous analysis of multi-components are also possible. Thus, it is not too much to say that the present method excels the others as a system of analysis.

The invention is illustrated below in further detail with reference to Examples, but the invention is not limited to these examples.

EXAMPLE 1

A synthetic pulp obtained by flush-spinning of high-density polyethylene was sulfonated with chlorosulfonic acid. The resulting sulfonated polyethylene pulp had an ion exchange capacity of 2.4 meq/g. A blend of 60 parts by weight of the synthetic pulp obtained above and 40 parts by weight of a natural pulp was formed into a web to prepare a sheet of filter paper, about 1 mm in thickness and 350 g/m$^2$ in basis weight. Through the filter paper, was passed 1 N HCl at a rate of 10 ml/minute for 15 minutes. The thus treated filter paper was purified by washing three times with distilled water. A circular piece, 47 mm in diameter, was cut out of the purified filter paper and mounted on a filter holder.

Four sample solutions of varied concentrations were prepared by dissolving $(NH_4)_2SO_4 \cdot FeSO_4 \cdot 6H_2O$ in distilled water and diluting to various concentrations. The four sample solutions had $Fe^{++}$ concentrations of 9.2, 6.5, 3.1, and 1.4 ppm, respectively, as measured by the method of atomic absorption.

Through the filter paper mounted on a filter holder, was passed distilled water twice and then 100 ml of the sample solution in about 10 minutes. The space velocity in this procedure corresponded to about 360 hr$^{-1}$. Thereafter, the filter paper was removed from the holder and dried. The same procedure was repeated to obtain four pieces of filter paper loaded with varied amounts of $Fe^{++}$. $Fe^{++}$ was not detected in the filtrate by the atomic absorption analysis (that is, the concentration of $Fe^{++}$ in the filtrate was below the detection limit of 0.05 ppm).

The filter paper loaded with $Fe^{++}$ was subjected to X-ray fluorescence analysis to measure Fe-K $\alpha$ line, from which $Fe^{++}$ was determined, under the conditions given below.

The same procedure as described above was repeated using aqueous solutions containing varied amounts of $Cu^{++}$. The measurement of Cu-K $\alpha$ line was carried out as mentioned above.

Conditions of X-ray fluorescence analysis:
Apparatus: Geigerflux SX of Rigaku Denki Co.
Crystal: LiF
Detector: scintillation counter
Path: vacuum (10$^{-1}$ mmHg)
Target: W or Mo The results obtained were as shown in FIG. 1. A linear relationship was found between the concentration and the intensity of X-ray fluorescence. Reproducibility of the analytical results was examined by repeating the above-said procedure five times, using a sample solution containing 6.5 ppm of $Fe^{++}$. The deviation in terms of intensity of X-ray fluorescence was below 2%. It was found that the quantitative analysis of $Fe^{++}$ and $Cu^{++}$ is possible by use of the lines in FIG. 1 as calibration lines. The time required for an analysis was 10 minutes for filtration, 10 minutes for drying, 30 minutes for X-ray fluorescence analysis, and 10 minutes for data reduction, making a total of only about 1 hours. When a circular piece, 47 mm in diameter, cut out of a commercial cation exchange membrane was immersed in 100 ml of the above-said sample solution containing $Fe^{++}$, adsorption of $Fe^{++}$ required 24 hours.

EXAMPLE 2

Standard sample solutions containing 0.1 to 1 ppm of $Zn^{++}$, $Cd^{++}$, or $Pb^{++}$ were prepared. In the same manner as in Example 1, each 100 ml of the standard solution was filtered through the filter paper. The atomic absorption analysis conducted on each filtrate indicated that each metal was completely collected by the filter paper, none of the metals having been detected in the filtrate.

X-ray fluorescence analysis was conducted on each dried filter paper (K$_\alpha$ line for $Zn^{++}$ and $Cd^{++}$ and L$_\alpha$ line for $Pb^{++}$). As shown in FIG. 2, sufficiently linear relationship was found to exist for each metal between the concentration of the sample solution and the intensity of X-ray fluorescence. Reproducibility of the analytical results was found to be satisfactory from the results of repeated tests performed on the same sample solution.

EXAMPLE 3

A cation exchange filter paper, 0.4 mm in thickness, was prepared from the same fiber as used in Example 1. Through the filter paper mounted on a filter holder, was passed 1 liter of an aqueous solution of mercury chloride containing 0.02 ppm of $Hg^{++}$ during an interval of about 10 minutes, followed by 20 ml of 1 N HCl and then by 30 ml of distilled water. The filtrate of 1 N HCl and that of distilled water were combined and analyzed by the method of atomic absorpton. By comparison with the calibration curve which had been separately plotted, it was found that more than 99% of $Hg^{++}$ in the sample solution had been collected and concentrated in the eluate. The time required for the analysis was about 30 minutes.

On the other hand, about 2 hours were required to concentrate by evaporation 1 liter of the same aqueous solution to 50 ml and about 2 hours and 10 minutes were required for an analysis to achieve the same result.

EXAMPLE 4

Using sulfonated polyethylene pulp having an ion exchange capacity of 0.5 meq/g, a cation exchange filter paper, 0.5 mm in thickness was prepared in the same manner as in Example 1. A circular piece, 47 mm in diameter, was cut out of the filter paper. This piece was 0.28 g in weight.

Through the piece of the filter paper mounted on a filter holder, was passed a solution having $Fe^{++}$ concentration of 20 ppm at the rate of 25 ml/minute. In this case, the linear velocity corresponds to about 90 cm/hr, and thus the space velocity (linear velocity/thickness) corresponds to about 1,800 hr$^{-1}$. When 50 ml of the sample solution was filtered, $Fe^{++}$ were not detected in the filtrate (less than 1 ppm) and all the $Fe^{++}$ were collected in the filter paper. However, when 1 l of the sample solution was filtered, the $Fe^{++}$ concentration in the filtrate was 19 ppm.

Then, at the rate of 250 ml/minute, the same procedure as above was repeated. The space velocity (linear velocity/thickness) therein corresponds to 18,000 hr$^{-1}$. In this case, even when 50 ml of the sample solution was filtered $Fe^{++}$ were detected in the filtrate.

What is claimed is:

1. A method for the rapid analysis of a cation contained in a liquid, which comprises filtering a liquid sample through a cation exchange filter paper having a high rate of ion exchange, which is composed of fibers having cation exchange functional groups, thus collecting in the top surface layer of said filter paper substantially the entire amount of the cation contained in said liquid sample, and analyzing the cation-loaded filter paper as such or the eluate obtained by elution of the objective cation from said cation-loaded filter paper to determine the cation.

2. A method according to claim 1, wherein each of the unit fibers composing the filter paper has a diameter of 0.5 to 100 $\mu$.

3. A method according to claim 1, wherein the filter paper is composed of fibers resistant to acids, alkalis, and solvents.

4. A method according to claim 1, wherein a starting material of the fiber is a pulp of polyethylene, polypropylene, polystyrene, or polyvinyl chloride.

5. A method according to claim 1, wherein the cation exchange functional group is sulfonic acid, carboxylic acid, phosphonic acid, sulfate ester, or phosphate ester group.

6. A method according to claim 1, wherein the cation exchange filter paper has an ion exchange capacity of 0.1 to 10 meq/g.

7. A method according to claim 1, wherein the cation exchange filter paper has a water permeability of 1 to 1,000 seconds, in terms of filtration time required to filter 1 cc of water under a head of 10 cm Aq through 1 cm$^2$ of filter paper.

8. A method according to claim 1, wherein the cation exchange filter paper has a thickness of 0.1 to 5 mm.

9. A method according to claim 1, wherein the space velocity of the liquid sample through the cation exchange filter paper is 1 to 10,000 hr$^{-1}$ in terms of linear velocity (cm/hr)/thickness (cm).

10. A method according to claim 1, wherein the analysis is carried out by the method of X-ray fluorescence analysis.

11. A method according to claim 10, wherein the space velocity of the liquid sample through the cation exchange filter paper is 1,000 hr$^{-1}$ or less.

12. A method according to claim 1, wherein the analyzing of the cation-loaded filter paper is carried out by measuring the cation in the eluate obtained by elution of the objective cation form said cation-loaded filter paper by means of the method of atomic absorption.

* * * * *